(12) United States Patent  
Murature et al.

(10) Patent No.: US 8,753,369 B2  
(45) Date of Patent: Jun. 17, 2014

(54) INTRAGASTRIC BALLOON RETRIEVAL MECHANISMS

(75) Inventors: Diego Murature, Santa Fe (AR); Janel A. Birk, Oxnard, CA (US); Frederick L. Coe, Santa Barbara, CA (US); Robert E. Hoyt, Jr., Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 465 days.

(21) Appl. No.: 12/712,112

(22) Filed: Feb. 24, 2010

(65) Prior Publication Data

US 2010/0168783 A1 Jul. 1, 2010

Related U.S. Application Data

(62) Division of application No. 11/450,665, filed on Jun. 9, 2006, now abandoned.

(51) Int. Cl.
*A61D 1/12* (2006.01)
*A61M 29/00* (2006.01)

(52) U.S. Cl.
USPC .............................. 606/192; 606/106; 606/191

(58) Field of Classification Search
CPC .............. A61F 5/0036; A61B 17/3468; A61B 2017/22035; A61B 2017/2217
USPC ................. 606/106, 216, 191, 192; 623/23.65
See application file for complete search history.

(56) References Cited

U.S. PATENT DOCUMENTS

| | | |
|---|---|---|
| 1,702,974 A | 2/1929 | MacDonald |
| 2,163,048 A | 6/1939 | McKee |
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders et al. |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

BIB Bioenterics Intragastric Balloon Program, "Take Control of Your Weight and Your Life/The Solution for You," Inamed Health, pp. 1-2; Jan. 19, 2004.

(Continued)

*Primary Examiner* — Katherine Dowe  
*Assistant Examiner* — Michael Mendoza  
(74) *Attorney, Agent, or Firm* — Gordon & Jacobson, PC

(57) ABSTRACT

A mechanism for removing a fluid-filled object from a patient. The apparatus includes a deflation tube with a puncture member at one end of the tube for piercing a hole in the object wall. The apparatus includes a retrieval mechanism slidable within the deflation tube lumen. The retrieval mechanism includes an expansion element that is expandable when positioned within the object from a first configuration with a dimension less than that of the deflation tube lumen to a second or deployed configuration with a dimension that is greater than an outer dimension of the puncture member. The expansion element contacts an inner surface of the inflatable object as the deflation tube and retrieval mechanism are withdrawn from the body cavity. The expansion element may be a T-bar, a foldable anchor, an inflatable member, or another expandable form.

20 Claims, 8 Drawing Sheets

(56) References Cited

U.S. PATENT DOCUMENTS

| | | | |
|---|---|---|---|
| 4,118,805 A | 10/1978 | Reimels | |
| 4,430,392 A | 2/1984 | Kelley et al. | |
| 4,485,805 A | 12/1984 | Foster, Jr. | |
| 4,545,367 A | 10/1985 | Tucci | |
| 4,592,355 A | 6/1986 | Antebi | |
| 4,598,699 A | 7/1986 | Garren et al. | |
| 4,607,618 A | 8/1986 | Angelchik | |
| 4,636,213 A | 1/1987 | Pakiam | |
| 4,694,827 A | 9/1987 | Weiner et al. | |
| 4,723,547 A | 2/1988 | Kullas et al. | |
| 4,881,939 A | 11/1989 | Newman | |
| 4,930,535 A | 6/1990 | Rinehold | |
| 4,969,899 A | 11/1990 | Cox, Jr. | |
| 5,074,868 A | 12/1991 | Kuzmak | |
| 5,084,061 A | 1/1992 | Gau et al. | |
| 5,211,371 A | 5/1993 | Coffee | |
| 5,226,429 A | 7/1993 | Kuzmak | |
| 5,289,817 A * | 3/1994 | Williams et al. | 600/204 |
| 5,449,368 A | 9/1995 | Kuzmak | |
| 5,527,340 A | 6/1996 | Vogel | |
| 5,601,604 A | 2/1997 | Vincent | |
| 5,658,298 A | 8/1997 | Vincent et al. | |
| 5,693,014 A | 12/1997 | Abele et al. | |
| 5,725,507 A | 3/1998 | Petrick | |
| 5,748,200 A | 5/1998 | Funahashi | |
| 5,819,749 A | 10/1998 | Lee et al. | |
| RE36,176 E | 3/1999 | Kuzmak | |
| 5,938,669 A | 8/1999 | Klaiber et al. | |
| 6,074,341 A | 6/2000 | Anderson et al. | |
| 6,102,678 A | 8/2000 | Peclat | |
| 6,102,897 A | 8/2000 | Lang | |
| 6,102,922 A | 8/2000 | Jakobsson et al. | |
| 6,152,922 A * | 11/2000 | Ouchi | 606/47 |
| 6,290,575 B1 | 9/2001 | Shipp | |
| 6,454,699 B1 | 9/2002 | Forsell | |
| 6,454,785 B2 | 9/2002 | De Hoyos Garza | |
| 6,464,628 B1 | 10/2002 | Forsell | |
| 6,470,892 B1 | 10/2002 | Forsell | |
| 6,503,264 B1 | 1/2003 | Birk | |
| 6,511,490 B2 | 1/2003 | Robert | |
| 6,547,801 B1 | 4/2003 | Dargent et al. | |
| 6,579,301 B1 | 6/2003 | Bales et al. | |
| 6,629,776 B2 | 10/2003 | Bell et al. | |
| 6,733,512 B2 | 5/2004 | McGhan | |
| 6,733,513 B2 | 5/2004 | Boyle et al. | |
| 6,746,460 B2 | 6/2004 | Gannoe et al. | |
| 6,840,257 B2 | 1/2005 | Dario et al. | |
| 6,994,095 B2 | 2/2006 | Burnett | |
| 7,020,531 B1 | 3/2006 | Colliou et al. | |
| 7,037,344 B2 | 5/2006 | Kagan et al. | |
| 7,056,305 B2 | 6/2006 | Garza | |
| 7,214,233 B2 | 5/2007 | Gannoe et al. | |
| 2002/0095181 A1 | 7/2002 | Beyar | |
| 2002/0139208 A1 | 10/2002 | Yatskov | |
| 2002/0183782 A1 | 12/2002 | Tsugita et al. | |
| 2003/0073880 A1 | 4/2003 | Polsky et al. | |
| 2003/0106761 A1 | 6/2003 | Taylor | |
| 2005/0055039 A1 | 3/2005 | Burnett et al. | |
| 2005/0131485 A1 | 6/2005 | Knudson et al. | |
| 2005/0190070 A1 | 9/2005 | Rudduck et al. | |
| 2005/0192615 A1 | 9/2005 | Torre et al. | |
| 2005/0240279 A1 | 10/2005 | Kagan et al. | |
| 2005/0250979 A1 | 11/2005 | Coe | |
| 2005/0261711 A1* | 11/2005 | Okada et al. | 606/153 |
| 2005/0267595 A1 | 12/2005 | Chen et al. | |
| 2005/0267596 A1 | 12/2005 | Chen et al. | |
| 2006/0020278 A1 | 1/2006 | Burnett et al. | |
| 2006/0025799 A1 | 2/2006 | Basu | |
| 2006/0069403 A1 | 3/2006 | Shalon et al. | |
| 2006/0142700 A1 | 6/2006 | Sobelman et al. | |
| 2006/0229702 A1 | 10/2006 | Agnew | |
| 2007/0016262 A1 | 1/2007 | Gross et al. | |
| 2007/0083224 A1 | 4/2007 | Hively | |
| 2007/0135829 A1 | 6/2007 | Paganon | |
| 2007/0147170 A1 | 6/2007 | Hood et al. | |
| 2007/0156248 A1 | 7/2007 | Marco et al. | |
| 2007/0173881 A1 | 7/2007 | Birk et al. | |
| 2007/0288033 A1 | 12/2007 | Murature et al. | |
| 2008/0172079 A1 | 7/2008 | Birk | |
| 2008/0208240 A1 | 8/2008 | Paz | |
| 2008/0243071 A1 | 10/2008 | Quijano et al. | |
| 2008/0255601 A1 | 10/2008 | Birk | |
| 2009/0131968 A1 | 5/2009 | Birk | |
| 2009/0259246 A1 | 10/2009 | Eskaros et al. | |
| 2010/0087843 A1 | 4/2010 | Bertolote et al. | |
| 2010/0100079 A1 | 4/2010 | Berkcan et al. | |
| 2010/0168783 A1 | 7/2010 | Murature et al. | |
| 2010/0174307 A1 | 7/2010 | Birk | |
| 2010/0274194 A1 | 10/2010 | Sobelman et al. | |

FOREIGN PATENT DOCUMENTS

| | | |
|---|---|---|
| DE | 8804765 | 5/1989 |
| DE | 102007025312 | 11/2008 |
| EP | 1396242 | 3/2004 |
| EP | 1396243 | 3/2004 |
| EP | 1774929 | 4/2007 |
| EP | 2095798 | 9/2009 |
| FR | 2797181 | 2/2001 |
| FR | 2823663 | 10/2002 |
| FR | 2852821 | 10/2004 |
| FR | 2855744 | 12/2004 |
| FR | 2941617 | 8/2010 |
| GB | 2086792 A | 5/1982 |
| JP | 63-279854 | 11/1988 |
| JP | 64-49572 | 2/1989 |
| JP | 1049572 A | 2/1989 |
| JP | 63-264078 | 10/1998 |
| WO | WO 00/15158 | 3/2000 |
| WO | WO 01/10359 | 2/2001 |
| WO | WO 01/49245 | 7/2001 |
| WO | WO01/66166 A2 | 9/2001 |
| WO | WO02/35980 A2 | 5/2002 |
| WO | WO03/055419 A1 | 7/2003 |
| WO | WO 03/105732 | 12/2003 |
| WO | WO 2004/019671 | 3/2004 |
| WO | WO 2005/007231 | 1/2005 |
| WO | WO 2006/020370 | 6/2006 |
| WO | WO 2006/063593 | 6/2006 |
| WO | WO2006/090018 | 8/2006 |
| WO | WO 2006/118744 | 11/2006 |
| WO | WO 2007/011086 | 10/2007 |
| WO | WO 2010/042062 | 4/2010 |

OTHER PUBLICATIONS

BIB Bioenterics Intragastric Balloon Program, "Taking the Next Step/Take Control of Your Weight and Your Life," Inamed Health, pp. 1-9; Apr. 29, 2004.

BIB Data Sheet Directions for Use, "BioEnterics Intragastric Balloon System," Inamed Health, 1-12 pp.

"Living With the Bib/BioEnterics Intragastric Balloon Program," Inamed Health; 1-10 Patient Information Brochure; pp.; May 1, 2005.

Baggio et al. "Biology of Integrins: GLP-1 and GIP"; Gastroenrology; V. 132; pp. 2131-2157; 2007.

Berne et al.; "Physiology"; V. 5; pp. 55-57, 210, 428 540, 579, 584, 591; 2004.

Boulant et al.; "Cholecystokinin in Transient Lower Oesophageal Sphincter Relation Due to Gastric Distension in Humans"; Gut; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Chaudri, Owais; "Can Gut Hormones Control Appetite and Prevent Obesity?" Diabetes Care, V. 31, Supp. 2, Feb. 2008.

Cohen et al.; "Oxyntomodulin Suppresses Appetite and Reduces Food in Humans"; J. Clin. Endocrinol. Metab.; V. 88; pp. 4696-4701; 2003.

Dakin et al.; "Oxyntomodulin Inhibits Food Intake in the Rat"; Endocrinology; V. 142; pp. 4244-4250; 2001.

(56) References Cited

OTHER PUBLICATIONS

Davison, J.; "Activation of Vagal-Gastric Mechanoreceptors by Cholecystokinin"; Proc. West. Pharmocol. Soc.; V. 29; pp. 363-366; 1986.

Ekblad et al.; "Distribution of Pancreatic Peptide and Peptide-YY"; Peptides; V. 23; pp. 251-261; 2002.

Greenough et al.; "Untangling the Effects of Hunger, Anxiety and Nausea on Energy Intake During Intravenous Cholecystokinin Octapeptide (CCK-8) Infusion" Physiology and Behavior; V. 65 (2); pp. 303-310; 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; "Gastrointestinal Factors in Hunger and Satiety"; Neurosci. and Behav. Rev.; V. 6; pp. 145-164; 1982.

Kissileff et al.; "Peptides that Regulate Food Intake: Cholecystokinin and Stomach Distension Combine to Reduce Food Intake in Humans"; Am. J. Physiol. Regul. Integr. Comp. Physiol.; V. 285; pp. 992-998; 2003.

Naslund et al.; "Prandial Subcutaneous Injection of Glucagon-Like Peptide"; Br. J. Nutr.; V. 91; pp. 439-446; 2004.

Renshaw et al. "Peptide YY: A Potential Therapy for Obesity"; Current Drug Targets; V. 6; pp. 171-179; 2005.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; 2001.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

Dakin et al.; "Peripheral Oxyntomodulin Reduces Food Intake and Body Weight gain in Rats" Endocrinology; V. 145; pp. 2687-2695; 2004.

\* cited by examiner

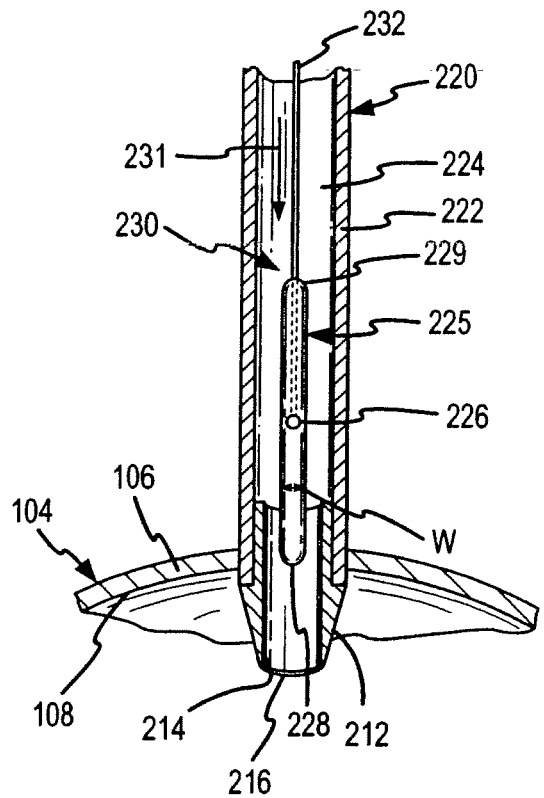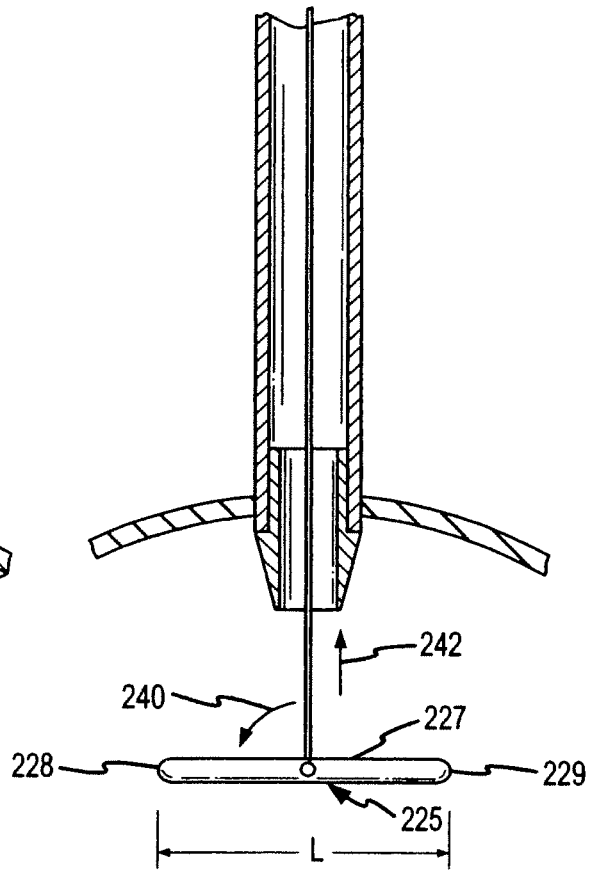
FIG.2A
FIG.2B
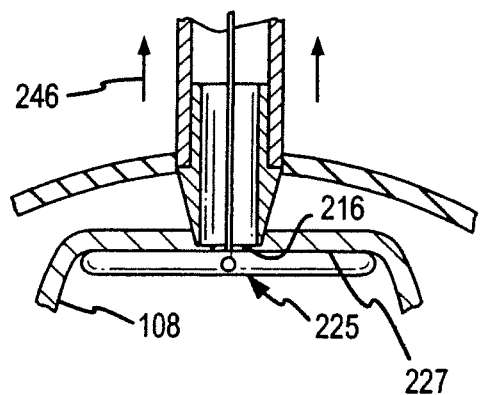
FIG.2C

INTRAGASTRIC BALLOON RETRIEVAL MECHANISMS

RELATED APPLICATION

This is a divisional of U.S. patent application Ser. No. 11/450,665, filed on Jun. 9, 2006 now abandoned, the entire disclosure of which is incorporated herein by this specific reference.

BACKGROUND OF THE INVENTION

1. Field of the Invention

The present invention relates, in general, to the use of an intragastric balloon and similar fluid-filled objects in treating obesity, and more particularly, to the devices and systems for endoscopical deflating and removing or retrieving such intragastric balloons and/or other fluid-filled objects from the stomachs of patients.

2. Relevant Background

Intragastric balloons, such as that described in U.S. Pat. No. 5,084,061 or other balloons and objects commercially available, are designed for providing short-term therapy for moderately obese individuals who need to shed pounds in preparation for surgery or as part of a dietary and behavioral modification program. A challenge with such balloons or fluid-filled objects is their removal after completion of therapy.

A typical intragastric balloon is a made of a silicone elastomer shell that is inserted into the stomach of a patient and then filled with fluid. For example, commercially available intragastric balloons are filled with saline solution or air but other fluids may be used in some situations. The intragastric balloon functions by partially filling the stomach, which enhances appetite control. Placement and filling of the intragastric balloon is completed non-surgically with a surgeon or doctor using an endoscope, gastroscope, or other device that is adapted for viewing internal cavities of a patient and with lumen or hollow channels for passing the retrieval instruments. Placement of intragastric balloons is temporary, and intragastric balloons are typically removed after six to twelve months.

Historically, endoscopic deflation and extraction of intragastric balloons has been an arduous task due to the difficulty associated with manipulating the balloon within the stomach. One method of removing the balloon involves several steps, each with its own tool. A sharp-ended puncture device, sometimes called a "killer," is inserted through the working channel of an endoscope to puncture the balloon. The puncture device is then removed, and the saline solution is either allowed to enter the stomach cavity, or removed via an aspiration tube inserted through the working channel and into the balloon. Finally, a grasping device or "grasper" having prongs, teeth, or a wire loop is inserted through the working channel to snag or snare the outside surfaces of the balloon. Once the outside of the balloon is hooked or grasped, the grasping device is used to pull the balloon through the esophagus as the gastroscope is removed. Other tools have been developed that provide a single tool that can pierce the balloon's shell, evacuate the fluid to deflate the balloon, and grasp or hook the outer surfaces of the balloon.

Even with these efforts, the retrieval of untethered intragastric balloons or other fluid-filled objects from a patient's stomach continues to present problems and can be a difficult task. The outer surface of the balloons is coated with gastric fluids in the stomach and tends to be very slippery or slick, which makes it difficult for even a relatively sharp grasper tool to grasp the balloon. One technique for addressing this issue is described in U.S. Pat. No. 5,084,061 and includes providing a retrieval tab on the outer surface of the balloon. A tool with a hook, loop, or snare then has to be latched onto the tab to allow retrieval. This technique has not been widely adopted as it requires specially manufactured balloons or objects with the external tab and also requires that the balloon be manipulated within the patient's stomach to find and align the tab with the hook on the removal tool, and this is often difficult to perform endoscopically (e.g., with limited tool dexterity and in limited visibility and light provided by the endoscope).

Therefore, it is desirable to provide an endoscopic device for removing an intragastric balloon in which the above mentioned disadvantages are substantially overcome.

Hence, there remains a need for an improved tool for supporting deflation and retrieval of intragastric balloons and other fluid-filled objects from the stomach of patients. Preferably, such a tool would be useful with existing medical systems or tools such as endoscopes and would provide quicker and more effective grasping or capture of the balloon or object to better support out-patient procedures.

SUMMARY OF THE INVENTION

The present invention addresses the above problems by providing a system and method for removing fluid-filled objects, such as intragastric balloons, from a body cavity of a patient. In contrast to prior devices that grasp the outer surfaces of an object, the removal system of the present invention includes a retrieval mechanism that can be inserted within the object via a lumen of the device used to deflate or aspirate the object contents (e.g., an aspirator tube or the like). The retrieval mechanism includes an expansion element that can be compressed or provided in a first configuration that allows it to readily pass through the deflation tube lumen but that expands to a second or deployed configuration when it is positioned within the unrestricted space within the interior of deflated object to be removed. The second or deployed configuration of the expansion element is typically significantly larger than the outer dimensions of the deflation tube, and as a result, surfaces of the expansion element contact the inner surfaces of the object when the retrieval mechanism is withdrawn from the body cavity, thereby capturing and removing the object. The expansion element may take numerous forms, as discussed in detail herein, such as, but not limited to, a T-bar, a foldable anchor, an inflatable member, a spring retriever, an elongate body with tabbed ends, an expandable tubular body, and a rollable or collapsible cone.

More particularly, an apparatus is provided for removing an inflatable object from a body cavity of a patient. The apparatus includes an aspiration or deflation tube with a lumen and a puncture member, such as a hollow needle, at one end of the tube for piercing a hole in the wall of the inflatable object. The puncture member includes a lumen that is in fluid communication or is fluidly coupled with the deflation tube lumen. The apparatus further includes a retrieval mechanism that can be slid within the deflation tube lumen. Significantly, the retrieval mechanism includes an expansion element that is expandable when positioned within the inflatable object from a first configuration with a dimension less than that of the deflation tube lumen to a second or deployed configuration with a dimension measured transverse to the deflation tube lumen that is greater than an outer dimension of the puncture member. In this second or deployed configuration, the expansion element has at least one contact surface (e.g., a surface extending transverse to an axis of the puncture member lumen) that contacts an inner surface of the inflatable object proximate to the hole formed in the wall of the inflatable object as the deflation tube and retrieval mechanism are withdrawn from the body cavity.

According to another aspect of the invention, a method is provided for evacuating and removing a fluid-filled object positioned in a body cavity. The method includes positioning an aspirator device in the body cavity and piercing a wall of the fluid-filled object with the aspirator device that includes a tube with a lumen, e.g., the piercing results in a portion of the tube passing through the shell wall and providing access to the interior of the object via the lumen. The method continues with advancing a retrieval mechanism into the lumen of the aspirator tube. The retrieval mechanism includes an expansion element that has a deployed configuration that is greater in size than the outer diameter of the aspirator tube, and the advancing includes extending the expansion element at least partially out of the lumen and into the pierced object. The expansion element then expands to its deployed configuration, and then the retrieval mechanism is withdrawn along with the aspirator device, which results in the expansion element contacting an inner surface of the object wall to cause the object to be removed from the body cavity along with the retrieval mechanism.

The retrieval mechanism typically also includes a flexible deployment member (such as a wire, wire rope, flexible tube, or the like) that is attached to the expansion element. The expansion element may take a number of forms, and for example, it may be selected from: a T-bar, an object inflated during the expanding of the expansion element, a folding anchor device that unfolds to the deployed configuration, a spring element that returns to an at-rest position during the expanding of the expansion element, an elongate body with tabs attached at opposite ends, a tubular body with slits cut in a spaced-apart manner, parallel to a longitudinal axis of the tubular body and with a tensioning wire attached to an end of tubular body, and a funnel collapsible into a cylinder and expandable into a frustoconical shape in the deployed configuration.

BRIEF DESCRIPTION OF THE DRAWINGS

FIGS. 2A-2C illustrate in more detail the "T-bar" retrieval mechanism shown in the system of FIG. 1 as it is being used to grasp and remove an object after deflation;

DETAILED DESCRIPTION OF THE PREFERRED EMBODIMENTS

Figure 1:
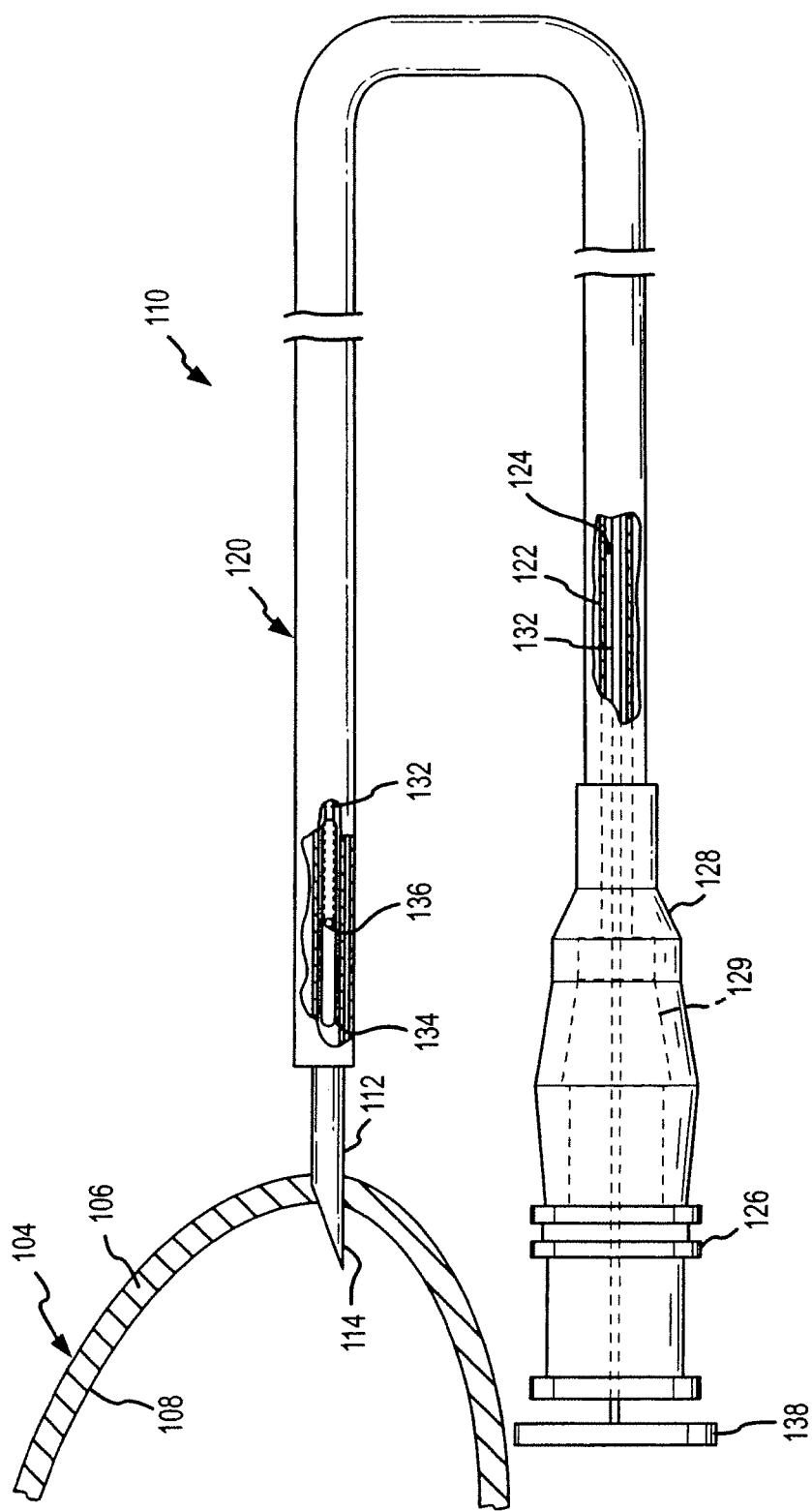
FIG. 1 illustrates a partial cutaway view of an inflatable object retrieval system according to one embodiment that is useful for deflating and removing a fluid-filled object such as an intragastric balloon from the stomach or other cavity of a patient.

The present invention is directed to methods and systems for retrieving fluid-filled objects from stomachs or other cavities of patients. The following description describes particularly systems and their operations for deflating, engaging or grasping, and retrieving or removing intragastric balloons from the stomach of a patient, but the concepts are equally applicable to nearly any object or hollow shape that is inflatable with fluid. Intragastric balloon retrieval systems of the invention are described as being useful with standard endoscopes, gastroscopes or the like that include a working channel through which the retrieval system can be passed to a stomach of a patient. Further, in a typical embodiment, the retrieval systems include a device for puncturing the shell of the intragastric balloon and for inserting an end of a tube, or an outlet of a lumen in such tube, within the intragastric balloon. The lumen can be used to deflate or aspirate the contents of the balloon. Then, during balloon retrieval procedures, a retrieval mechanism of the invention is inserted through the lumen (or is passed further through the lumen in embodiments in which the mechanism remains in the lumen during deflation).

Significantly, each embodiment of the retrieval mechanisms of the invention includes an expansion or grasping element at or proximal to its distal end that is inserted through the lumen of the deflation tube so as to extend beyond the tip or end of the deflation tube (or beyond a needle, prong, or other component used to pierce the balloon shell). These expansion elements each are adapted to contact and engage the inner surface of the intragastric balloon as the retrieval mechanism and the deflation or aspiration tube is withdrawn from the stomach of the patient. Typically, each expansion member is capable of taking on a first profile or dimensions (deployment configuration or profile) smaller than or equal to the inner diameter of the lumen such that it can pass through the deflation or aspiration tube. When in the open or unrestricted space within the intragastric balloon, the expansion element expands to a second profile or dimensions (deployed or retrieval configuration or profile) substantially greater than the outer diameter of the needle and/or tube.

This larger-sized profile or configuration and the contact surface(s) of the expansion element allow the expansion element to effectively contact or "grasp" the inner surface of the balloon adjacent to the hole that was previously formed in the balloon shell by the needle or puncture member of the retrieval mechanism. In some cases, the "grasping" includes trapping or pinching balloon material near the formed hole between the contact surfaces of the expansion element and the outer surfaces of the needle or puncture member or deflation tube. These and other features of the invention will become clear from the following description of the retrieval systems of the invention and the multiple embodiments of retrieval mechanisms useful in such systems to contact the inner surface of intragastric balloons so as to grasp or capture the balloons for efficient retrieval from a patient.

FIG. 1 illustrates an inflatable/deflatable object removal system 110 of the invention that is particularly well suited for use when the object is an intragastric balloon. The object removal system 110 includes a single lumen tubing 120 that is configured with an outer wall 122 that has a diameter such that the tube 120 is small enough to pass through a working channel or lumen of an endoscope, gastroscope, or the like (not shown). The tube wall 122 defines a lumen 124 that extends from one to the other end of the tube 120. At the distal end, a needle or puncture member 112, such as a hollow cannulated needle with a relatively sharp tip 114, is provided, which may be an extension of the tube 120 or a separate component that is attached to the tube wall 122. The puncture member 112 optionally has its lumen or hollow center coupled to the lumen 124 or other channel through the tube 120 such that fluid (not shown) can be aspirated from an object or balloon 104 that has its shell or wall 106 pierced by the tip 114 of the member 112.

During deflation operations, the fluid contained by the inner surfaces 108 of the balloon wall 106 may be allowed to flow into the stomach or cavity of a patient, but often it is desirable to aspirate or evacuate the fluid via the tube 120. In this regard, the insertion of the needle member 112 results in the lumen 124 provided in the tube 120 being exposed to the interior space of the balloon 104 defined by the inner surface 108 of the balloon wall 106 (e.g., via the needle member 112 depending upon how deep the tube 120 is inserted into the balloon 104). To facilitate insertion and later deflation of the balloon 104, a connector 126 (e.g., a luer connector or the like) is provided with a tube connector that is also hollow or has an internal channel 129 at the proximal end of the removal system 110. After the tube 120 is positioned in a patient and the tip 114 has pierced a balloon 104, the connector 126 can be connected to a suction mechanism to apply suction and evacuate fluid from the balloon 104 via needle 112 and lumen 124 of tube 120. While the system 110 is shown with the single lumen tube 120 and a particular connector and puncture arrangement, these components can be varied significantly to practice the invention such as with a dual lumen tube, a different connector, and a differing needle or piercing device, with an important feature of the aspirator portion being the ability to pierce the wall 106 and position a lumen port, opening, or end within the balloon 104 to provide access to the inner surface 108 of the wall 106.

A significant feature of the system 110 is the improved ability of the system 110 for grasping and retrieving the deflated balloon 104. To this end, the system 110 includes a retrieval mechanism (which is shown in more detail in FIGS. 2A-2C). The retrieval mechanism includes a deployment member 132 that may be a wire, a twisted wire rope, a flexible rod, a tube, or other component that is adapted for being pushed and pulled through the lumen 124 of the tube 120. As shown, the retrieval mechanism includes a handle 138 attached to the proximal end of the member 132 and an expansion element made up of a bar (or T-bar) 134 attached with connector 136 (such as a pin, solder or other connection). The handle 138 is used by an operator (such as doctor, surgeon, or other medical technician) to push the wire or member 132 until the distal end of the wire or member 132 and the bar 134 passes the tip 114 of the needle 112 and is positioned within the balloon 104. At this point (i.e., the deployed or fully deployed position), the expansion element is able to expand or convert from a first, smaller profile or configuration to a second, larger profile or configuration (e.g., a first profile with dimensions that allow the bar and wire 134 and 132 to fit within the lumen 124 and a second profile with dimensions that are larger than the tip 114 used to pierce the balloon wall 106). Because the expansion or conversion element is an important feature of the invention and system 110, the following figures and discussion emphasize a number of embodiments of retrieval mechanisms with varying expansion or conversion elements, with the tube 120 and other features of the system 110 being useful in combination with any of the retrieval mechanisms (and, as discussed earlier, the retrieval mechanisms being useful with removal systems other than that shown in FIG. 1).

FIGS. 2A-2C illustrate one embodiment of a retrieval mechanism 230 that may be used in a removal system, such as system 110 of FIG. 1. As shown, a deflation or aspiration tube 220 with a wall 222 defines a lumen 224 (such as a lumen with a circular or other shaped cross section). At the end of the tube 220 is a puncture or needle member 212 that is affixed to the tube wall 222 such as by threading and/or adhesive or the like. The tubing 220 and member 212 may be made of a number of materials to practice the invention such as flexible plastic or elastomer, e.g., PTFE, ETFE, or PDVF. With its outer dimensions being selected to be less than the inner diameter of an endoscope working channel, such as less than about 0.1 inches, this results in a lumen outer diameter less than this dimension, such as 0.08 inches, 0.05 inches, or less. The deploying or first profile or configuration of the retrieval mechanism 230 is selected to be less than the diameter of the lumen to allow its deployment into the balloon interior. Clearly, the specific dimensions are not limiting with the more important aspect being the relative dimensions.

The puncture member 212 is shown after it has been used to pierce the balloon 104 by making a hole in the wall 106. As shown, the outlet or tip 216 of the member 212 is within the balloon 104 such that the lumen or channel 214 of the member 212 is within the balloon 104. In FIG. 2A, the retrieval mechanism 230 is being deployed as shown at arrow 231 through the lumen 224 into the interior of the balloon 104. The retrieval mechanism 230 includes a deployment member 232 (e.g., a wire, wire rope, flexible rod, or the like made of metal or other materials), which is connected to a handle (not shown). An expansion element 225 is attached with connector 226 to the end of the deployment member 232. The expansion element 225 can be thought of as a T-bar and includes an elongate body of a width, W, with two opposing ends 228, 229 (shown curved in this embodiment but may take other shapes to practice the invention). The width, W, of the expansion element 225 is less than the lumen 224 and channel 214 in the puncture member 212. As shown, the expansion element 225 is collapsible onto the wire or deployment member 232 while it is being deployed through the lumen 224 of the tube 220. In other words, the bar or body of the expansion element 225 may be aligned with the wire 232 to fit into the tubing 220, and when emerging from the tubing 220 end 212 resumes a perpendicular orientation.

FIG. 2B illustrates the expansion element 225 in its deployed profile or configuration in which its body is perpendicular to (or at least no longer aligned with) wire 232. The expansion element 225 swings down as shown with arrow 240 to the deployed or second larger profile. The larger or second profile results in the body or expansion element 225 having a length, L, that is larger than the outer diameter of the puncture element 212, and the length, L, is typically significantly larger than this diameter (e.g., 2 to 6 or more times larger than this diameter) with the upper limitation being that the length of the extension element 225 as measured along the elongate body from end 228 to end 229 is less than the inner diameter of the channel through which the tube 220 and balloon 104 be removed, e.g., less than a patient's esophagus inner diameter such as less than about 0.75 inches). With this profile, the element 225 is longer than the hole formed in the balloon wall 104.

As shown, the extension element 225 has a contact or grasping surface 227. When the retrieval mechanism 230 is withdrawn or pulled back toward the tube 220 as shown at arrow 242, the contact surface 227 of the expansion element 225 contacts (engages or grasps) the inner surface 108 of the balloon wall 106. This grasping or contact by the expansion element 225 is shown in FIG. 2C. As shown, once the wire or deployment member 232 is pulled or withdrawn until the contact surface 227 abuts the tip or end 216 of the puncture member 212 (or pinches balloon wall 106), the tube 220 of the removal system is pulled or withdrawn as shown at arrows 246 to remove the balloon 104 along with the tube 220 and retrieval mechanism 230. The expansion element 225 is effective for grasping the balloon 104 by contacting the inner surface 108, and the balloon shell 106 can be pulled out of its environment (e.g., a stomach or other patient cavity) draped over the T-bar or elongate body of the expansion element 225.

Figure 3A:
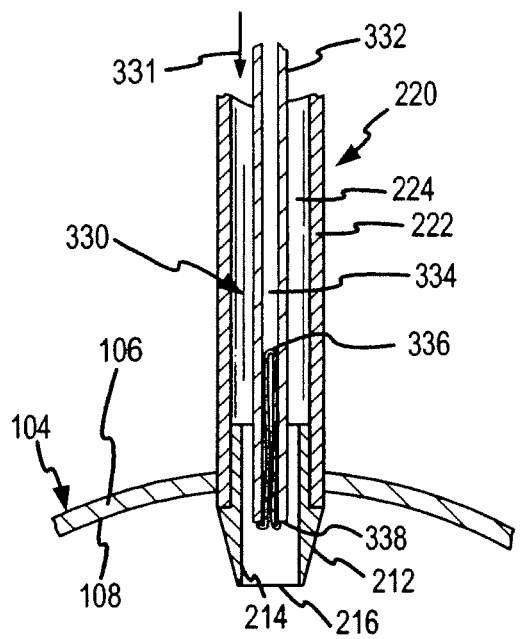
FIGS. 3A-3C illustrate similarly to FIGS. 2A-2C a retrieval mechanism according to the invention in which the expansion or grasper portion or element itself is inflatable and may be used in object retrieval systems such as that shown in FIG. 1.
Figure 3B:
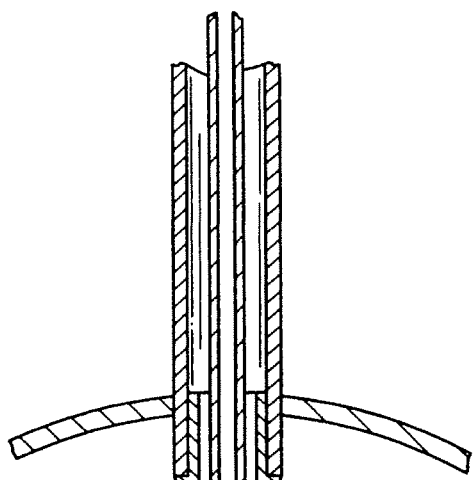
Figure 3C:
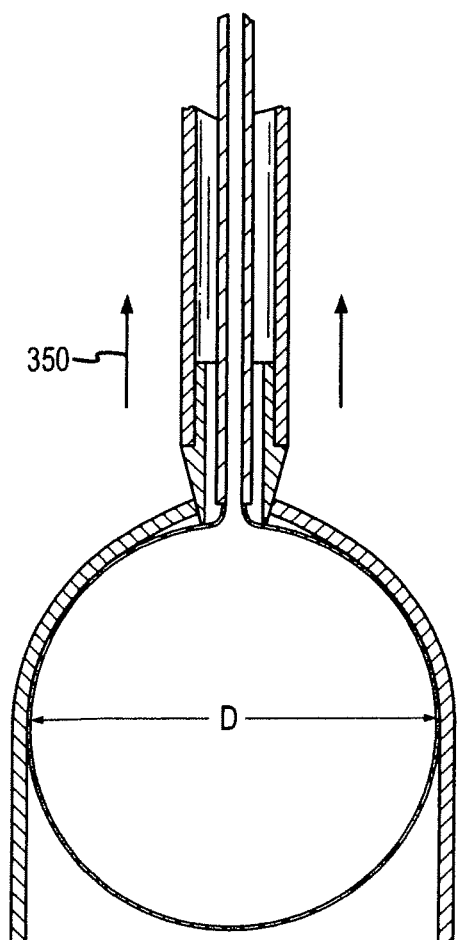

FIGS. 3A to 3C illustrate another embodiment of a retrieval mechanism 330 being deployed into a balloon 104 that has been pierced by tube 220 and puncture member 212 (with similar components shown in FIGS. 2A to 2C not being described in detail). The mechanism 330 can be thought of as using a balloon grasper to grasp the inner surface 108 of the balloon wall 106. Specifically, the retrieval mechanism 330 includes a tube of smaller diameter than the tube 220, and this tube is advanced as shown in FIG. 3A at arrow 331 through the lumen 224. At the end of the tube 332, a small balloon or inflatable expansion element 336 is provided in the lumen 334 of smaller tube 332. The expansion element 336 is attached at or near the end 338 of the tube 332.

As shown in FIG. 3B, the expansion element 336 includes a wall or shell 337 and an inner surface 339. When the expansion element 336 (or end 338 of tube 332) is positioned within the balloon 104 (or past the hole in wall 106), air or other fluid 344 is forced through the lumen 334 of tube (or deployment member) 332 to force the element 336 out of the tube 332 and to apply pressure against inner surface 339 of wall 337 and inflate the expansion element 336 as shown with arrows 348. The inflation of element 336 may be controlled by achieving a predetermined pressure in the lumen 334 and element 336 or by inserting a predetermined volume of gas or fluid 344. At FIG. 3C, the expansion element 336 is shown inflated to a second configuration or profile and an outer diameter, D, that is greater than the outer diameter of the puncture member 212 (and hole in wall 106), e.g., 10 times larger or the like. The outer surfaces of the wall 337 (e.g., contact surfaces of the expansion element 336) abut or engage the inner surface 108 of the balloon wall 106 when the tube 332 is withdrawn into the deployment tube 220 until the expansion element 336 hits or is adjacent to the tip 216 of the puncture member 212. The tube 220 can then be withdrawn to remove the deflated intragastric balloon 104 with the balloon shell 106 draped over the expansion element 336. Again the diameter, D, is selected to be larger than the outer diameter of the member 212 and smaller than the channel through which the tube 220 is removed from a patient's body, such as less than about 0.75 inches when the channel is a patient's esophagus. The wall 337 of the expansion element 336 may be formed from many elastic materials such as rubber or the like, and in some cases, the contact surface or outer surface of wall 337 is rough (or roughened) to improve the "grasping" of inner surface 108 of balloon 104.

Figure 4A:
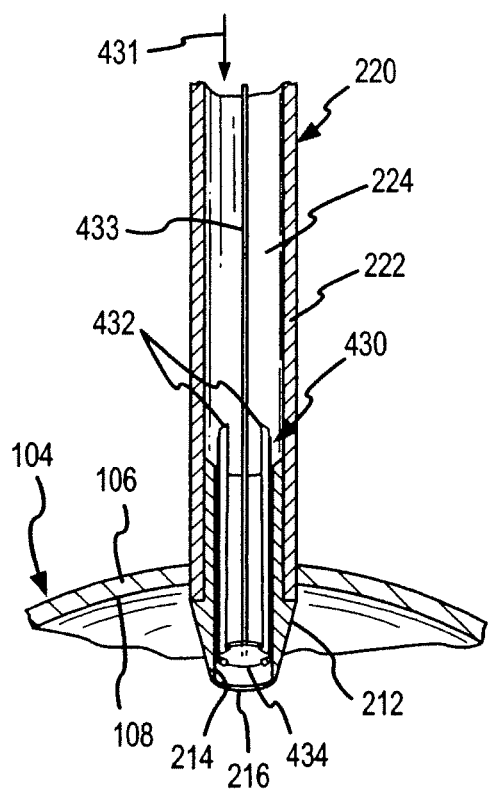
FIGS. 4A and 4B is another retrieval mechanism according to the invention that may be used with the system shown in FIG. 1 and that utilizes a "folding anchor" type of expansion or grasper element.
Figure 4B:
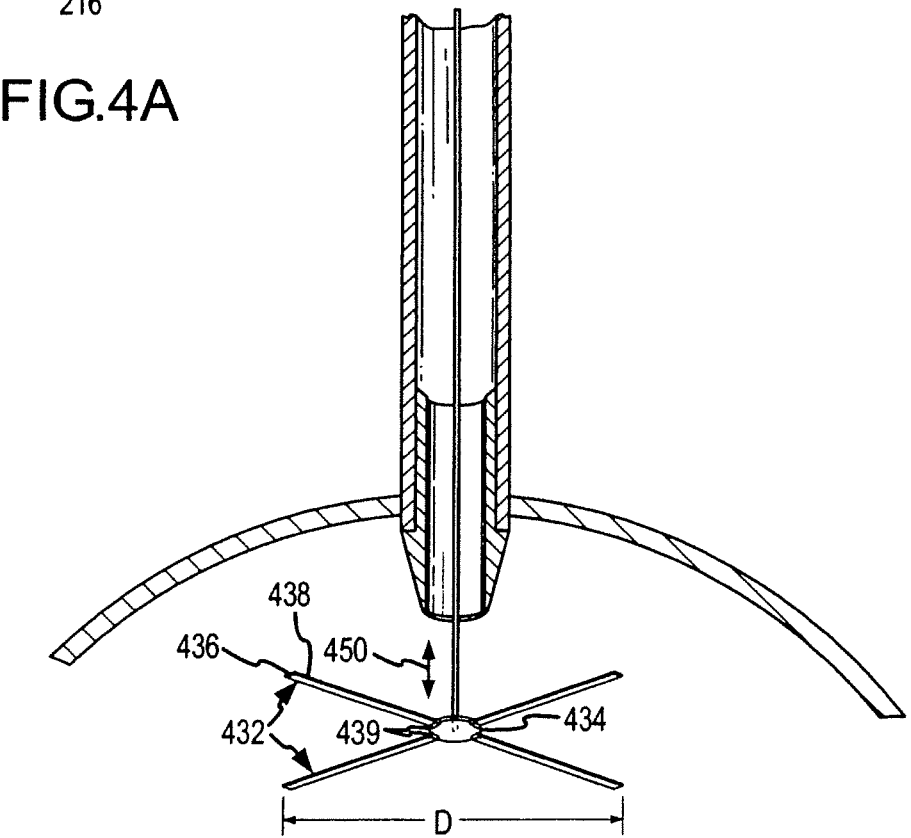

FIGS. 4A and 4B illustrate another embodiment of a retrieval mechanism 430 that includes an expansion element that can be thought of as a "folding anchor." FIG. 4A illustrates the expansion element in the first or deploying profile or configuration in which it has dimensions that are less than or equal to the inner diameter of the lumen 224 of tube 220. The expansion element includes a connector 434 attached to the end of deploying member 433. The connector 434 may be a circular disk or plate that and the member 433 may be a wire, a wire rope, or other flexible component. The expansion element further includes a number of anchor legs 432 (such as 3 or more) that are elongate bodies with two ends 436, 439 and a contact surface 438.

FIG. 4B illustrates how the legs 432 expand out or unfold/deploy when the expansion element is positioned beyond the tip 216 of puncture member 212 within the interior volume of the balloon 104 defined by shell 106. To this end, the legs are pivotally attached at ends 439 to the connector 434. In some embodiments, the legs and connector are formed such that the deployed or second profile shown in FIG. 4B is an "at rest" configuration (such as by forming the anchor expansion element as a single piece) and the unfolding is the result of the legs returning to their at rest position. As shown, though, the legs "fall" or pivot from their first configuration shown in FIG. 4A proximate to the deployment member 433 to the deployed or expanded, second configuration shown in FIG. 4B. In the fully deployed position of FIG. 4B, the expansion element of retrieval mechanism 430 has a "diameter" (or width), D, that is measured from the outer tip 436 of one leg 432 to an outer tip of an opposing leg. This diameter, D, again is significantly larger than the outer diameter of the tube 220 and/or puncture member 212 (e.g., such as 2 to 10 times or more larger) and less than a predetermined maximum value to allow removal from a patient. Then, as shown at arrow 450, the deployment member 433 is pulled back into the tube lumen 224 until the contact surface 438 of the legs 432 contacts the inner surface 108 of the balloon wall 106 when the connector abuts or is proximate to the tip 216 of member 212. Then, the tube 220 and deployment member 433 are withdrawn or pulled from the patient to retrieve the deflated balloon 104.

Figure 5A:
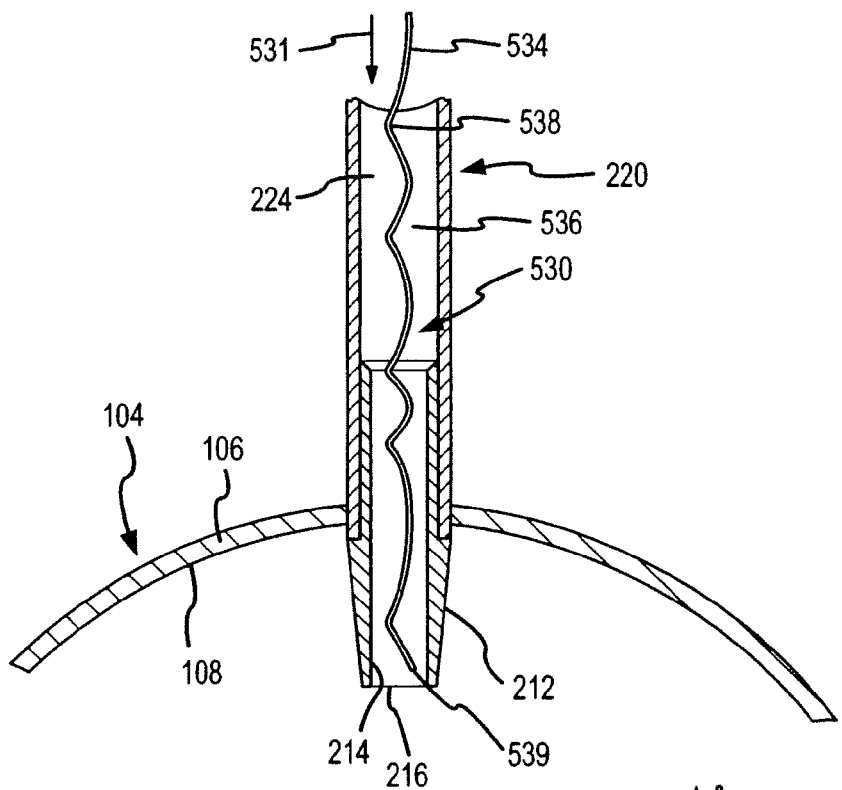
FIGS. 5A and 5B is yet another retrieval mechanism that may be used with the system of FIG. 1 and that includes an expansion or grasper element that is made up of a spring member that uncoils to its at rest configuration within the retrieved object.
Figure 5B:
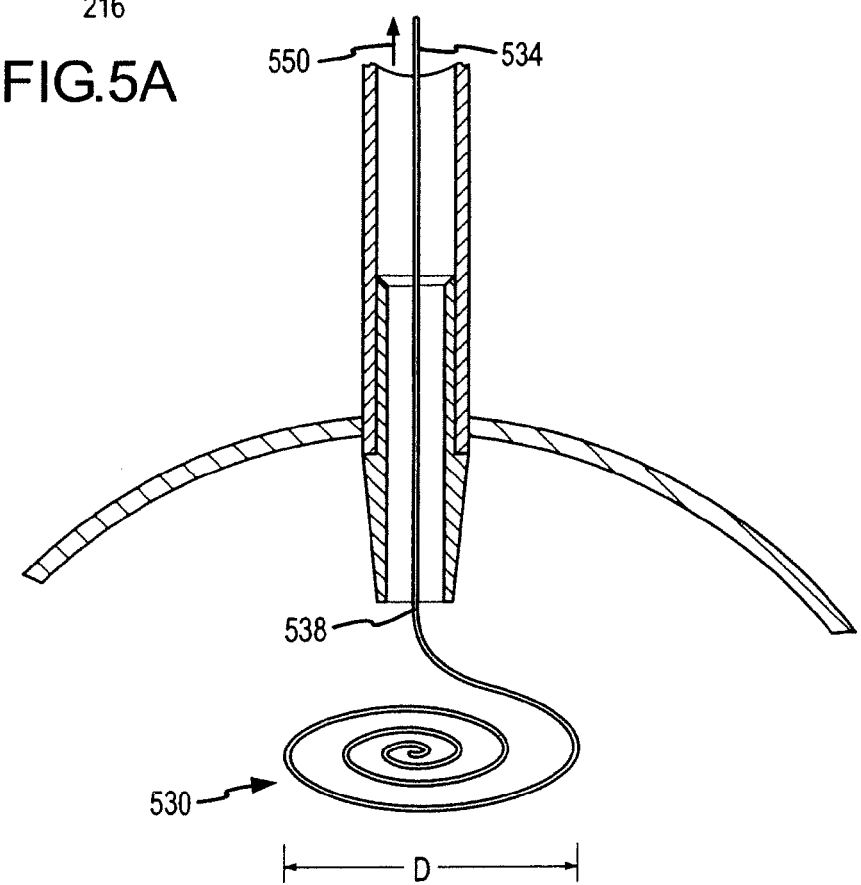

FIGS. 5A and 5B illustrate yet another retrieval mechanism 530 useful in object removal systems of the invention. With this retrieval mechanism 530, the aspirator tube 220 is again placed within the hollow shape or shell 106 of the object or balloon 104. The retrieval mechanism 530 is then advanced down the lumen 224 into the balloon 104. The retrieval mechanism 530 includes a deployment member (e.g., a wire or the like) 534 that is connected at a first end 538 to an expansion element 536. The other distal end 539 of the expansion element 536 is fed into the balloon 104. This embodiment of the retrieval mechanism 530 can be thought of as a "spring" embodiment as the expansion element 536 may be made up of a length of spring, a spring coil, spring wire, or the like that can be "straightened" into a first profile or configuration for feeding through the tube lumen 224 and then, when in an unrestricted space such as the interior space of the balloon shell 106, the expansion element spring 536 returns to its at rest or second profile or configuration.

The unrestricted or at rest configuration of the expansion element 536 can be defined as having an outer dimension, D (even if not a true circle or sphere) that is larger than the outer diameter of the puncture member 212 and/or tube 220 as shown in FIG. 5B (e.g., 2 to 10 or more times larger). As shown at arrow 550, the wire or deployment member 534 is withdrawn or pulled back up the lumen 224 of the tube 220 until the first or proximal end 538 of the expansion element 536 contacts or is pulled within the lumen 214 of the puncture member 212. At this point, the unrestricted spring, which has resumed its natural or at rest state of a coil, spiral, or other non-linear shape, may compress somewhat but is selected to have a stiffness (or resistance to leaving its at rest state) that allows it to contact the inner surface 108 of the balloon wall 106 and grasp the balloon 104. In other words, the expansion element 536 shown in FIG. 5B is selected such that forces applied by the deflated balloon inner surface 108 ("retraction forces") do not compress the element 536 to a point where its dimension, D, is less than the outer diameter of the member 212. As a result, the expansion element 536 is able to "grasp" or engage the inner surfaces 108 when the tube 220 is withdrawn from the hole in the wall 104, and the balloon shell 106 can be pulled out of its environment draped over the spring element 536.

Figure 6A:
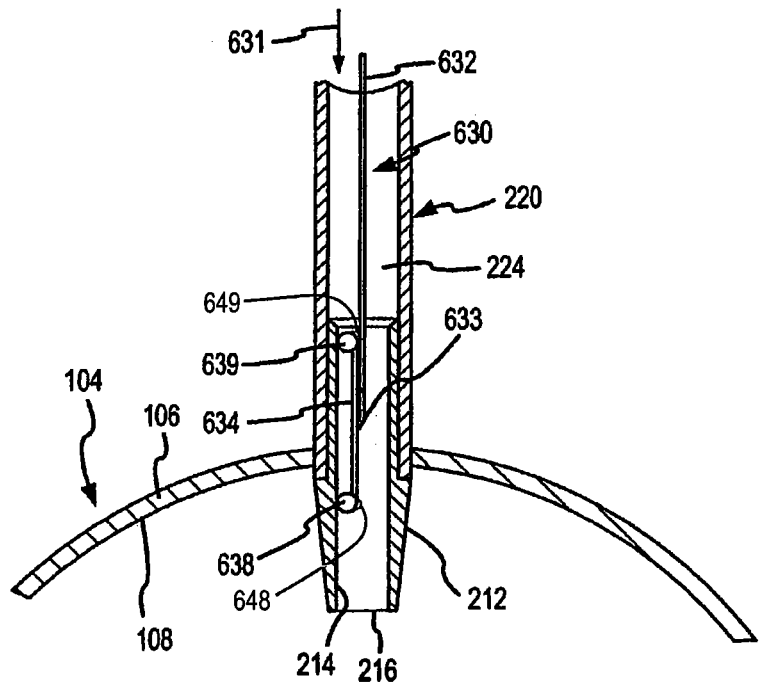
FIGS. 6A and 6B illustrate a retrieval mechanism with an expansion or grasper element similar to that shown in FIGS. 2A-2C that utilizes a plurality of tabs to engage the inner surface of an object being retrieved.
Figure 6B:
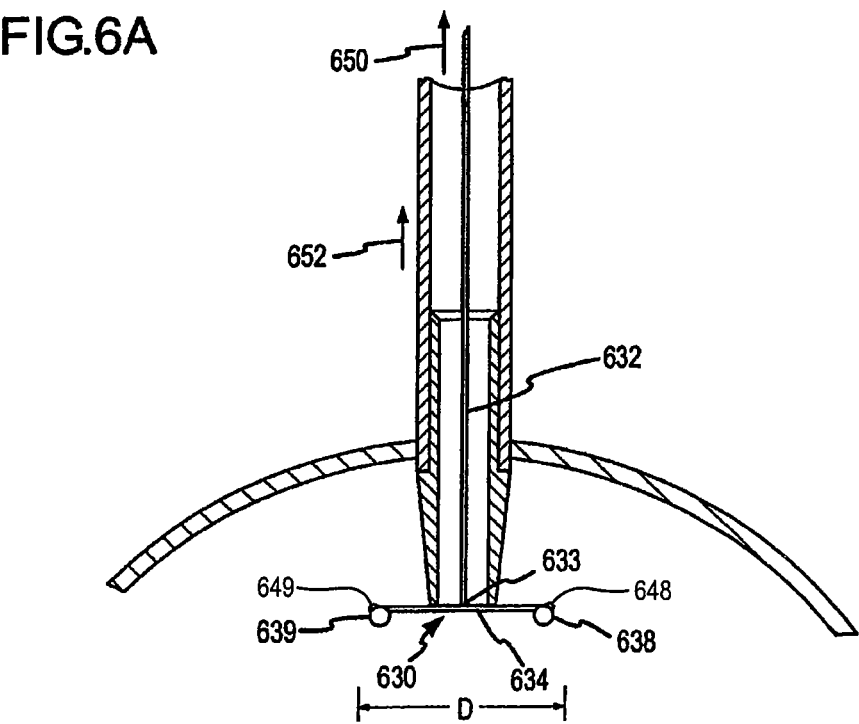

FIGS. 6A and 6B show another retrieval mechanism 630 with a "tab-based" expansion element. As shown by arrow 631, the tab expansion element is fed through the lumen 224 of the aspiration tube 220 with wire or deployment member 632. The member 632 is attached to the body 634 of the expansion element, and the body 634 can be aligned with the member 632 in a first, smaller profile or configuration of the expansion element. The elongated body 634 may be a relatively stiff or rigid tube or wire. On each opposite end of the body 634 is attached a tab or grasping member 638, 639. Each of these tabs 638, 639 may have a variety of shapes and be made of a variety of materials to practice the invention. As shown, the tabs 638, 639 are relatively planar and have a circular shape. In other cases, the tabs 638, 639 may be more spherical or hemispherical in shape or range toward planar but with a different shape such as square, rectangular, triangular, hyperbolic, or the like. The materials used for the body 634 and tabs 638, 639 may be the same (such as when these components are stamped out or formed as a unitary piece), may be selected for easy joining (such as soldering or the like), or may be different.

As shown in FIG. 6B, body 634 of the expansion element "expands" by swinging out of alignment with the wire 632, such as to a perpendicular or transverse position relative to the wire 632. This expanded or second, larger profile or configuration of the expansion element results in the expansion element having a dimension or width, D, that is larger than the outer diameter of the puncture element 212 and tube wall 222 (e.g., 2 to 8 times or more larger with the ratio of 5:1 being used in some embodiments). When the wire 632 is withdrawn into the lumen 224, a surface of the body 632 proximate to the wire 632 contacts the tip or end 216 of the puncture member 212. In this illustrated position, the tabs 638, 639 extend outward from the puncture member 212. When, as shown by arrow 652, the tube 220 and retrieval mechanism 630 are withdrawn, contact surfaces of the tabs 638, 639, which may include prongs 648, 649, contact or "grasp" the inner surfaces of the balloon shell 106. The contact surfaces of each tab 638, 639 are typically about the size of or less than the inner diameter of the tube lumen 224 or lumen 214 of the puncture element 212, whichever is less, to allow the tabs 638, 639 to be passed through the tube 220 and member 212 into the balloon 104. The balloon shell 104 can then be pulled out of its environment draped over the shaped extensions 638, 639 of the expansion element of the retrieval mechanism 630.

Figure 7A:
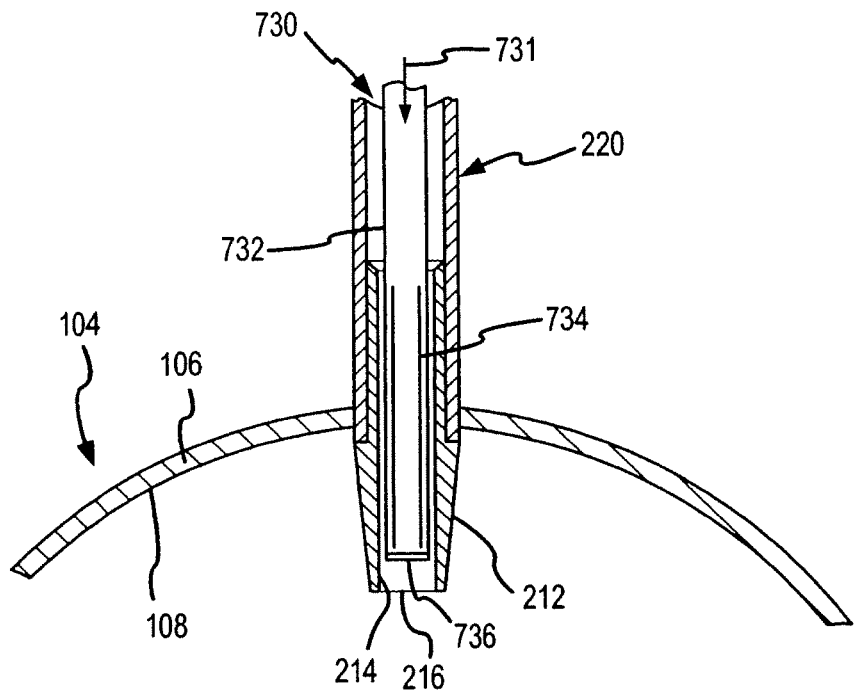
FIGS. 7A and 7B illustrates still another retrieval mechanism useful with the retrieval systems of the invention that includes yet another embodiment of an expansion or grasper element (e.g., an expandable tube tip) useful for grasping or engaging inner surfaces of a balloon or other inflatable/deflatable object.
Figure 7B:
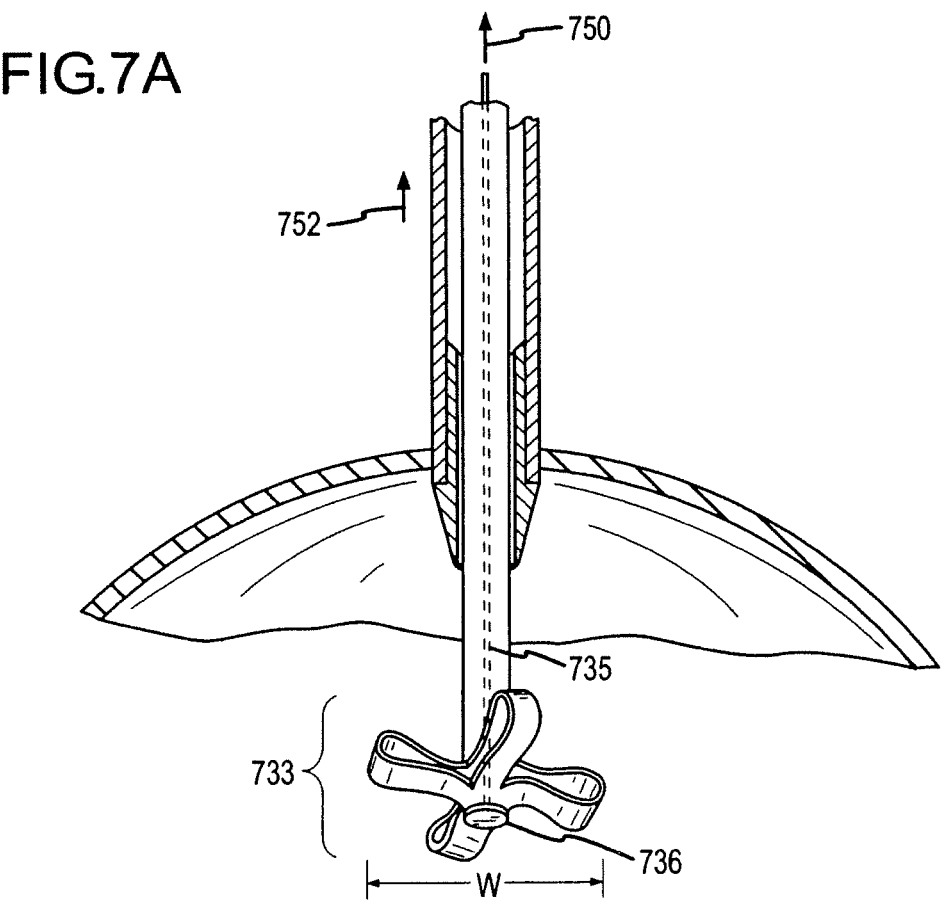

FIGS. 7A and 7B illustrate still another retrieval mechanism 730 useful with object removal systems of the invention. As shown, the expansion element 733 of the retrieval mechanism 730 can be though of as an expandable tube retriever or grasper. To this end, the retrieval mechanism 730 includes a hollow tube 732 of flexible plastic or elastomeric materials with an outer diameter less than the inner diameters of aspiration tube 220 and puncture member 212. The tube 732 can be passed or advanced as shown at arrow 731 in a deflated balloon 104. The tip or expansion element 733 includes a number of cut slits parallel to the axis of the tube 732, e.g., 4 slits spaced about 90 degrees apart about the circumference of the tip 733. The retrieval mechanism 730 further includes a wire 735 that is attached toward the distal end of the tip 733 such as to a plate 736 at or near the distal end of tip 733. When the expansion element or tip 733 is positioned within the shell 106 of the balloon 104, tension is applied as shown at arrow 750 to the wire or string 735 such that the attached end of the tip or plate 736 is pulled with the wire 735 toward the tube 220 or puncture member 212. This movement causes the expansion element 733 with the slits 734 to buckle and expand from the first small profile to a second profile (e.g., a cruciform shape or the like) with a width, W, that is larger than the outer diameter of the puncture member 212 and tube wall 222 (e.g., 2 to 5 or more times larger with a minimum ratio of 3.5:1 being used in some cases). The outer surfaces of the expansion element 733 then provide contact surfaces that contact the inner surface 108 of the balloon wall 106 when the retrieval mechanism 730 is pulled by wire 735 such that the expanded tip 733 abuts the puncture element 212 and the tube 220 is withdrawn as shown at 752.

FIGS. 8A to 8D illustrate a retrieval mechanism 830 that makes use of a funnel expansion element 834. The retrieval mechanism 830 includes a feed or deployment wire 832 that is used to deploy as shown at arrow 831 the expansion element 834, which is attached to the wire 832, through the lumen 224 of the aspiration tube 220. As shown by arrows 842 in FIG. 8B, the funnel expansion element 834 expands outward from its first profile that is smaller than the inner diameter of the tube 220 and puncture member 212 to its second profile with a width (or diameter), W, that is larger than the outer dimensions of the tube 220 and member 212. The expansion element 834 may include a circular plate 835 that is attached to the wire 832 and an expandable/retractable wall 836. The wall 836 may take a number of forms, and in one embodiment, is made of a plurality of vanes or ribs (such as elongate metal plates) that are wrapped about the wire 832. In this case, the wall 836 expands outward to width, W, and exposes interior surfaces 838 of the wall 836.

Figure 8A:
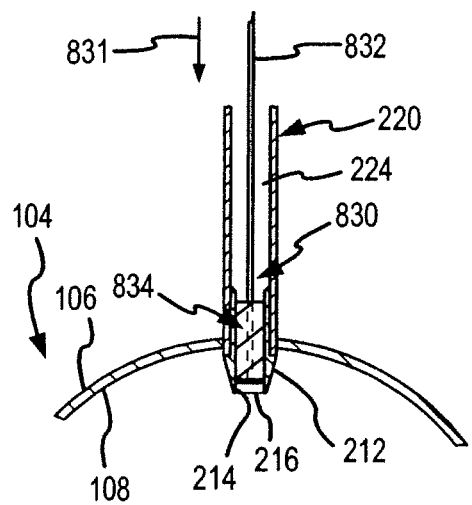
FIGS. 8A-8D illustrates a retrieval mechanism with a funnel-based expansion or grasper element.
Figure 8B:
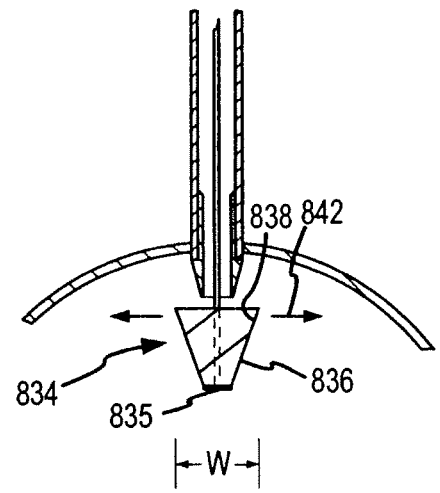
Figure 8C:
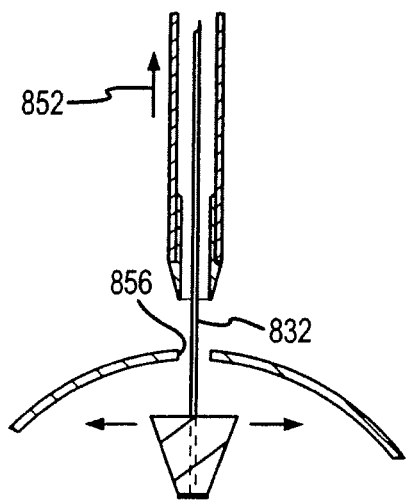
Figure 8D:
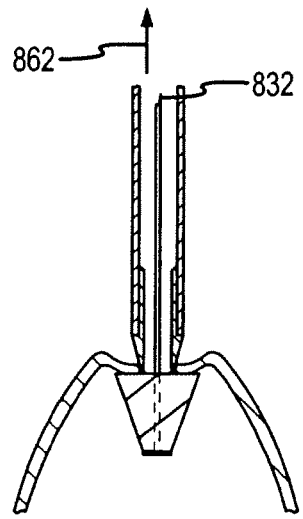

As shown by arrow 852 in FIG. 8C, the tube 220 is withdrawn from the balloon such that the wire 832 of the retrieval mechanism 830 extends through the hole 856 in the balloon wall 106 and the expansion element 834 remains in the balloon 104 (e.g., the tube 220 is withdrawn initially without withdrawing or tensioning the wire 832). Then, as shown by arrow 862 in FIG. 8D, tension is applied to the wire 832 of the retrieval mechanism 830 such that the funnel expansion element 834 moves toward the puncture member 212 and tube 220. The inner surface 108 of the balloon wall 106 is contacted by the upper edge of the wall 836 such that a portion of the balloon wall 106 is pinched or sandwiched between the inner surface 838 of the wall 836 of the expansion element 834 and the outer surfaces of the puncture member 212 and/or tube wall 222. Preferably, to support this grasping action, the shape of the wall 836 in the expanded or second configuration is selected to correspond to the conical shape of the exterior surfaces of the tip or puncture member 212 or end of tubing 220. When retracted, the balloon wall 106 is captured between the funnel expansion element 834 and the cone tip 212 with some force. The balloon shell 104 can then be pulled out of its environment by applying tension to the tube 220 and the wire 832 of the retrieval mechanism 830.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. For example, the body or bar 225 shown in FIGS. 2A to 2C may include a groove along one side for receiving the wire 232 when the expansion element is placed in the first profile for deploying through the aspiration tube. In other embodiments, the T-bar 225 can be attached by a loop at the end of the wire rather than being attached to the end of the wire 232. In the retrieval mechanism 430 of FIGS. 4A and 4B, the anchor legs 432 may have a curved (or concave) shape to increase their strength and the outer ends or tips 436 may be textured or include small prongs or the like for enhanced grabbing of the inner surface 108 of the balloon wall 106. Further, the tube expansion element 733 of FIGS. 7A and 7B can be "locked" in the expanded position, such as, for example, by providing a slot or recessed latching surface in the inner lumen walls of the tube 732. A bead or ball or other shape may be attached to the wire 735 within the tip 733 (such as proximal to the plate 736). When the bead or ball is pulled to the slot or recessed latching surface within the tip 733, the expansion element 733 becomes latched or locked in the cruciform or expanded profile.

We claim:

1. A method for evacuating and removing a fluid-filled object positioned in a body cavity of a patient, comprising:
    positioning an aspirator device in the body cavity;
    piercing a wall of the fluid-filled object with the aspirator device, wherein the aspirator device comprises a tube with a lumen;
    sliding a retrieval mechanism in the lumen of the tube, wherein the retrieval mechanism comprises a deployment member and an expansion element pivotally coupled to an end of the deployment member, the expansion element having a deployed configuration greater in size than an outer diameter of the tube and wherein the sliding comprises extending the expansion element at least partially out of the lumen and into the pierced wall of the object;
    expanding the expansion element to the deployed configuration by extending the expansion element at least partially out of the lumen, the expansion element expanding to the deployed configuration when emerging from the lumen of the tube; and
    withdrawing the retrieval mechanism and the aspirator device from the body cavity, wherein during the withdrawing the expansion element contacts an inner surface of the wall of the object, forcing the object to be removed from the body cavity with the retrieval mechanism.

2. The method of claim 1, further comprising applying tension on the deployment member prior to the withdrawing to force the expansion element to abut a tip fixed on the tube.

3. The method of claim 1, wherein the expansion element is selected from a group consisting of (a) a T-bar, (b) a folding anchor device that unfolds to the deployed configuration and (c) an elongate body with tabs attached at opposite ends.

4. The method of claim 1, wherein the deployment member is selected from a group consisting of (a) a wire, (b) a twisted wire rope, (c) a flexible rod and (d) a tube.

5. The method of claim 1, wherein the expansion element includes a groove for receiving the deployment member prior to the expanding of the expansion element.

6. The method of claim 1, wherein the expansion element is connected by a loop at the end of the deployment member.

7. The method of claim 1, wherein the expansion element has a curved shape.

8. The method of claim 1, wherein the expansion element is textured for enhanced contact with the inner surface of the wall of the object.

9. The method of claim 1, wherein the expansion element includes a prong located on a surface of the expansion element for enhanced contact with the inner surface of the wall of the object.

10. A method for evacuating and removing a fluid-filled object positioned in a body cavity of a patient, comprising:
    positioning a deflation device in the body cavity;
    piercing a wall of the fluid-filled object with the deflation device, wherein the deflation device comprises a tube with a lumen;
    sliding a retrieval mechanism in the lumen of the tube, wherein the retrieval mechanism comprises an expansion element having a compressed configuration when confined within the lumen of the tube and an at-rest configuration when not confined within the lumen of the tube, the at-rest configuration greater in size than an outer diameter of the tube and wherein the sliding comprises extending the expansion element at least partially out of the lumen and into the pierced wall of the object;
    expanding the expansion element from the compressed configuration to the at-rest configuration by extending the expansion element at least partially out of the lumen of the tube and into the pierced wall of the object, the expansion element configured to resume a substantially perpendicular orientation with the tube when not confined within the lumen of the tube; and
    withdrawing the retrieval mechanism and the deflation device from the body cavity, wherein during the withdrawing the expansion element contacts the object from within the object and pinches the object against the deflation device, forcing the object to be removed from the body cavity with the retrieval mechanism.

11. The method of claim 10, wherein the expansion element is selected from a group consisting of (a) a length of spring, (b) a spring coil, (c) a spring wire and (d) a folding anchor device that unfolds to the at-rest configuration.

12. The method of claim 10, wherein the expansion element includes a groove for receiving the deployment member prior to the expanding of the expansion element.

13. The method of claim 10, wherein the expansion element has a curved shape.

14. The method of claim 10, wherein the expansion element is textured for enhanced contact with the inner surface of the wall of the object.

15. The method of claim 10, further comprising a prong disposed on a surface of the expansion element for enhanced contact with the inner surface of the wall of the object.

16. A method for evacuating and removing an intragastric balloon from a stomach of a patient, comprising:
    positioning a deflation device in the stomach;
    piercing a wall of the intragastric balloon with the deflation device, wherein the deflation device comprises a tube with a lumen;
    sliding a retrieval mechanism in the lumen of the tube, wherein the retrieval mechanism comprises a deployment member and an expansion element coupled to an end of the deployment member, the expansion element having a deployed configuration greater in size than an outer diameter of the tube and wherein the sliding comprises extending the expansion element at least partially out of the lumen and into the pierced wall of the intragastric balloon;

expanding the expansion element to the deployed configuration after the expansion element has extended at least partially out of the lumen and into the pierced wall of the intragastric balloon; and withdrawing the retrieval mechanism and the deflation device from the stomach, wherein during the withdrawing the expansion element contacts an inner surface of the wall of the intragastric balloon at a first location and the deflation device contacts an outer surface of the wall of the intragastric balloon at a second location adjacent the first location, forcing the intragastric balloon to be removed from the stomach with the retrieval mechanism via sandwiching the wall of the intragastric balloon at the first location and the second location.

17. The method of claim 16, wherein the tensioning member is selected from a group consisting of (a) a wire, (b) a twisted wire rope, (c) a flexible rod and (d) a tube.

18. The method of claim 16, wherein the expansion element includes a groove for receiving the deployment member prior to the expanding of the expansion element.

19. The method of claim 16, wherein the expansion element has a curved shape.

20. The method of claim 16, wherein the expansion element is selected from a group consisting of (a) a T-bar, (b) a folding anchor device that unfolds to the deployed configuration and (c) an elongate body with tabs attached at opposite ends.

\* \* \* \* \*